(12) United States Patent
Lim et al.

(10) Patent No.: US 6,228,130 B1
(45) Date of Patent: *May 8, 2001

(54) PRIMARY INTERMEDIATE IN OXIDATIVE HAIR DYEING

(75) Inventors: Mu-Ill Lim, Trumbull; Linas R. Stasaitis, Fairfield; Yuh-Guo Pan, Stamford; Michael Y. M. Wong, Easton, all of CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/185,019

(22) Filed: Nov. 3, 1998

(51) Int. Cl.$^7$ .......................... A61K 7/13; C07C 211/00; C07C 209/00

(52) U.S. Cl. .......................... 8/406; 8/405; 8/407; 8/408; 8/409; 8/410; 8/411; 564/306; 564/418

(58) Field of Search .................. 8/405–412; 564/306, 564/418

(56) References Cited

U.S. PATENT DOCUMENTS

| | | | |
|---|---|---|---|
| Re. 30,199 | 1/1980 | Rose et al. | 8/10.2 |
| 5,421,833 | 6/1995 | Lorenz | 8/410 |
| 5,529,584 | 6/1996 | Audousset et al. | 8/412 |
| 5,538,516 | 7/1996 | Audousset et al. | 8/412 |
| 5,599,353 | 2/1997 | Cotteret et al. | 8/412 |
| 5,620,484 | 4/1997 | Maubru | 8/409 |
| 5,690,695 | 11/1997 | Cotteret et al. | 8/409 |
| 5,735,908 | 4/1998 | Cotteret | 8/410 |
| 5,814,106 | * 9/1998 | Audousset | 8/409 |
| 5,980,584 | * 11/1999 | Lim et al. | 8/408 |

FOREIGN PATENT DOCUMENTS

| | | | |
|---|---|---|---|
| 4335623 | 4/1995 | (DE) | A61K/7/13 |
| 4335625 | 4/1995 | (DE) | A61K/7/13 |
| 4434494 | 3/1996 | (DE) | A61K/7/13 |
| 705598 | 4/1996 | (EP) | A61K/7/13 |
| 706787 | 4/1996 | (EP) . | |
| 2730926 | 8/1996 | (FR) | A61K/7/13 |
| 727203 | 8/1996 | (EP) . | |
| 728463 | 8/1996 | (EP) . | |
| 2239265 | 7/1992 | (GB) | A61K/7/13 |

\* cited by examiner

*Primary Examiner*—Russell Travers
*Assistant Examiner*—Shengjun Wang
(74) *Attorney, Agent, or Firm*—Charles J. Zeller

(57) ABSTRACT

5-Nitroisatin is reacted with sodium hydroxide to produce an α-keto acid sodium salt that is reduced with borane-tetrahydrofuran complex and then hydrogenated to produce 1-(2,5-diaminophenyl)ethylene glycol, a novel compound useful as a primary intermediate in the production of oxidative hair dyes.

14 Claims, No Drawings

PRIMARY INTERMEDIATE IN OXIDATIVE HAIR DYEING

FIELD OF THE INVENTION

The invention relates to 1-(2,5-diaminophenyl)ethylene glycol (1), to a process for preparing same and to its use in compositions for dyeing human hair.

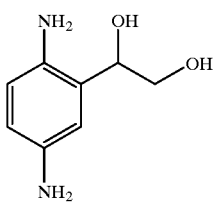

BACKGROUND OF THE INVENTION

Compositions for the oxidative dyeing of hair comprise primary intermediates (such as p-phenylenediamine, p-toluenediamine, p-aminophenol, 4-amino-3-methylphenol) and couplers (such as resorcinol, 2-methylresorcinol, 3-aminophenol, 5-amino-2-methylphenol). A majority of shades have been produced with dyes based on p-phenylenediamine. However, as noted in U.S. Pat. Nos. 5,599,353 and 5,538,516, the use of p-phenylenediamine is being questioned for toxicological reasons, mainly due to its sensitization potential.

Because of the supposed toxicological issues attendant to its use, the art has been looking for substitutes for p-phenylenediamine.

EP 400,330 B1 (GB 2,239,265 A) describes the use of 2-(2-hydroxyethyl)-p-phenylenediamine as a replacement for p-phenylenediamine.

Pyrimidine derivatives, such as tetraaminopyrimidine, have been also suggested as alternatives to p-phenylenediamine (see U.S. Pat. No. Re. 30,199 [U.S. Pat. No. 4,003,699]). However, GB 2,239,265 A, points out that although the use of pyrimidine derivatives as developers has reduced toxicological problems, the pyrimidine derivatives are not completely satisfactory with respect to coloring performance.

U.S. Pat. No. 5,421,833 discloses hair dye compositions asserted to be without sensitizing potential. The dye compositions are disclosed to possess improved dyeing properties for all shades. The compositions comprise only 2-(2'-hydroxyethyl)amino-5-aminotoluene in combination with the usual coupling agents (with the exclusion of 1-methoxy-2,4-diaminobenzene and 1-ethoxy-2,4-diaminobenzene).

The object of the present invention was to develop a p-phenylenediamine alternative having less sensitization potential. This proved to be a difficult task. Since the structure-sensitization relationship is not known, it is difficult to predict whether a hair dye molecule will exhibit much lower potential for sensitization than p-phenylenediamine. Surprisingly and unexpectedly, we have found that 1-(2,5-diaminophenyl)ethylene glycol is a much weaker sensitizer than p-phenylenediamine.

SUMMARY OF THE INVENTION

The present invention provides the novel compound, 1-(2,5-diaminophenyl)ethylene glycol, a process for preparing same, its use as a primary intermediate in oxidative hair dyeing, and hair dye compositions containing same.

In contrast to p-phenylenediamine, 1-(2,5-diaminophenyl)ethylene glycol was surprisingly found to be a weak sensitizer.

Current technology generally requires p-phenylenediamine or p-toluenediamine for producing red and black shades (see U.S. Pat. No. 5,538,516).

The present invention enables one skilled in the art to formulate a natural black shade and dark red shade through the use of 1-(2,5-diaminophenyl)ethylene glycol without relying on p-phenylenediamine (see Table 2).

Advantageously, the shades obtained through use of 1-(2,5-diaminophenyl)ethylene glycol have good wash and light fastness.

The process for the preparation of the 1-(2,5-diaminophenyl)ethylene glycol is new and commercially feasible. The synthesis of the compound 1 requires three steps: (1) ring-opening of 5-nitroisatin with sodium hydroxide, (2) borane reduction of the keto acid, and (3) hydrogenation.

1-(2,5-Diaminophenyl)ethylene glycol has excellent solubility in water. Four grams of 1-(2,5-diaminophenyl)ethylene glycol sulfate salt completely dissolves in 100 ml of water at room temperature. The p-toluenediamine sulfate salt is partially soluble under the same conditions. Water solubility is important because hair dye formulations employed for hair coloring are in large part water.

DETAILED DESCRIPTION OF THE INVENTION

The following examples are intended to illustrate the present invention and not to limit same in any respect. It should be noted that where percentage is employed, unless indicated to the contrary, it is percent by weight and is based on total weight.

1. The synthesis of 1-(2,5-diaminophenyl)ethylene glycol (compound 1):

The synthesis of compound 1 was carried out according to the following scheme.

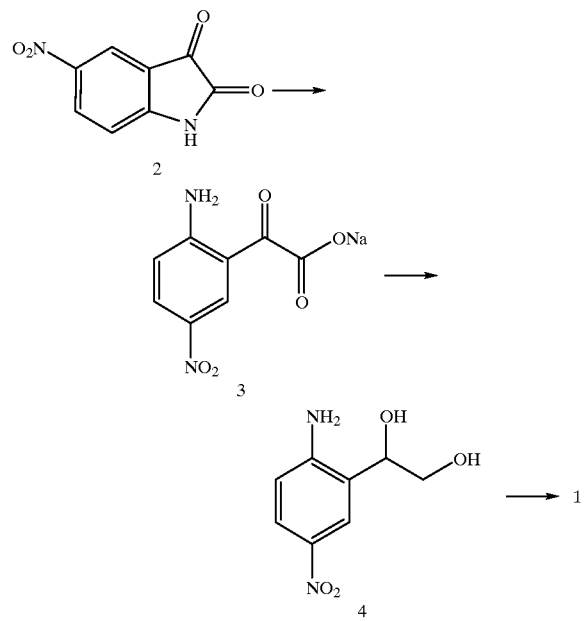

A solution of 5-nitroisatin, compound 2, (96.07 g, 500 mmole) with sodium hydroxide solution (200 mL, 5.5 M solution) in ethanol (200 mL) was stirred at room temperature for 1 hour. The resulting solid was collected and washed with acetone to give compound 3 (116.71 g, 100% yield): mp 281° C. decomposed; $^1$H NMR (300 MHz, DMSO-$d_6$) δ 6.80 (d, 1H, J=9.3 Hz), 8.01 (dd, 1H, J=9.3, 2.7 Hz), 8.46 (d, 1H, J=2.7 Hz), 8.75 (bs, 2H).

Borane-THF (1.0M, 1.2 L) was added dropwise over a period of 2.5 hours to a stirred suspension of the α-keto acid sodium salt (3) (92.86 g, 400 mmole) in 400 mL tetrahydrofurane (THF) at 4° C. After the borane addition was complete, the reaction mixture was warmed to ambient temperature and stirred for 16 hours. The excess borane was quenched at 4° C. with methanol and the reaction mixture was evaporated under vacuum. The residue was dissolved in 400 mL water and acidified to pH 2–3 with concentrated hydrochloric acid. The resulting precipitate was collected and air-dried to afford compound 4 (78.15 g, 98.6% yield): mp 154–156° C.: $^1$H NMR (300 MHz, DMSO-$d_6$) δ 3.44 (m, 2H), 4.65 (q, 1H, J=10, 4.8 Hz), 4.70 (t, 1H, J=6.0 Hz), 5.47 (d, 1H, J=4.2 Hz), 6.47 (s, 2H), 6.62 (d, 1H, J=9.0 Hz), 7.84 (dd, 1H, J=9.0, 2.7 Hz), 8.04 (d, 1H, J=2.7 Hz); MS m/z 198 (M$^+$).

A mixture of compound 4 (21.80 g, 110 mmole) and 10% Pd/C (2.2 g) in CH$_3$OH/acetic acid (150/15 mL) was hydrogenated at 60 psi for 2.5 hours. The mixture was filtered over a layer of Celite and washed with methanol. The combined filtrate was neutralized with concentrated ammonium hydroxide. The resulting precipitate was filtered to give the compound 1 (15.11 g, 81.8% yield): mp 153–154° C.; $^1$H NMR (300 MHz, DMSO-$d_6$) δ 3.40 (m, 2H), 4.12 (s, 2H), 4.17 (s, 2H), 4.49 (t, 1H, J=6 Hz), 4.60 (s, 1H), 5.05 (s, 1H), 6.24 (dd, 1H, J=8.1, 2.7 Hz), 6.35 (d, 1H, J=8.1 Hz), 6.44 (d, 1H, J=2.4 Hz); MS m/z 168 (M$^+$).

2. Compositions

Dye compositions containing 1-(2,5-diaminophenyl) ethylene glycol can also contain other primary intermediates and couplers.

It should be noted that for certain dark shades, including dark brown and black shades, it is desirable to include a meta diamine as one of the couplers. Suitable meta diamines include m-phenylenediamine, 2,4-diaminophenoxyethanol and 4,6-bis(2-hydroxyethoxy)-m-phenylenediamine.

Suitable primary intermediates include:

p-Phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis(2-hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-bis(N-hydroxyethyl)-N-(4-aminophenyl)amino-2-propanol and 2-methyl-4-dimethylaminoaniline;

p-Aminophenol derivatives such as: p-aminophenol; p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; 5-aminosalicylic acid and 1-(4-amino-2-hydroxyphenyl)-ethane-1,2-diol;

Ortho-developers such as: catechol; pyrogallol; o-aminophenol; 2,4-diaminophenol; 2,4,5-trihydroxytoluene; 1,2,4-trihydroxybenzene; 2,3-dihydroxynaphthalene; 5-methyl-o-aminophenol; 6-methyl-o-aminophenol and 2-amino-5-acetaminophenol and;

Heterocyclic derivatives such as: 2,4,5,6-tetraaminopyrimidine; 4,5-diamino-1-methyl-pyrazole and 2-dimethylamino-5-aminopyridine;

Suitable couplers include:

Phenols, resorcinol and naphthol derivatives such as: 1,7-dihydroxynaphthalene; resorcinol; 4-chlororesorcinol; 1-naphthol; 2-methyl-1-naphthol; 1-acetoxy-2-methyl naphthalene; 1,5-dihydroxynaphthalene; 2,7-dihydroxynaphthalene; hydroquinone; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone and 1-naphthol-4-sulfonic acid;

m-Phenylenediamines such as: m-phenylenediamine; 2,4-diaminophenoxyethanol; N,N-bis(2-hydroxyethyl)-m-phenylenediamine; 2,6-diaminotoluene; 2-N,N-bis(hydroxyethyl)-2,4-diaminophenetole; bis(2,4-diaminophenoxy)-1,3-propane; 1-hydroxyethyl-2,4-diaminobenzene; 2-amino-4-hydroxyethylaminoanisole; 1-aminoethoxy-2,4-diaminobenzene; 2,4-diaminophenoxyacetic acid; 4,6-bis(hydroxyethoxy)-m-phenylenediamine; 2,4-diamino-5-methylphenetole; 2,4-diamino-5-hydroxyethoxytoluene; 2,4-dimethoxy-1,3-diaminobenzene and 2,6-bis(hydroxyethylamino)-toluene;

m-Aminophenols such as: m-aminophenol; 2-hydroxy-4-carbamoylmethylamino toluene; m-carbamoylmethyl- aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethoxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol and Heterocyclic derivatives such as: 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(2-hydroxyethoxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine.

Preferred primary intermediates include:

p-Phenylenediamine derivatives such as: p-toluenediamine; p-phenylenediamine; N-2-methoxyethyl-p-phenylenediamine; N,N-bis(2-hydroxyethyl)-p-phenylenediamine; 2-hydroxyethyl-p-phenylenediamine;

p-Aminophenol derivatives such as: p-aminophenol; p-methylaminophenol; 3-methyl-p-aminophenol; 2-methoxymethyl-p-aminophenol and 1-(5-amino-2-hydrxphenyl)-ethane-1,2-diol;

Ortho-developers such as: o-aminophenol; 1,2,4-trihydroxybenzene; 2-ethylamino-p-cresol; 5-methyl-2-aminophenol; 6-methyl-2-aminophenol and 2-amino-5-acetaminophenol and Heterocyclic derivatives such as: 2,4,5,6-tetraaminopyrimidine and 4,5-diamino-1-methylpyrazole.

Preferred couplers include:

Phenols, resorcinol and naphthol derivatives such as: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol and thymol (2-isopropyl-5-methylphenol);

m-Phenylenediamines such as: m-phenylenediamine; 2,4-diaminophenoxyethanol; 1,3-bis(2,4-diaminophenoxy) propane; 2-amino-4-hydroxyethylamino anisole and 4,6-bis(hydroxyethoxy)-m-phenylenediamine;

m-Aminophenols such as: m-aminophenol; 6-hydroxybenzomorpholine; 2-hydroxy-4-aminotoluene; 2-hydroxy-4-hydroxyethylaminotoluene and 2-methyl-m-aminophenol and Heterocyclic derivatives such as: 4,5-diamino-1-methyl-pyrazole; 2-dimethylamino-5-aminopyridine; 1-phenyl-3-methyl-5-pyrazolone; 3,4-methylenedioxyphenol; 3,4-methylenedioxyaniline; 4-hydroxyindole; 5,6-dihydroxyindole; 7-hydroxyindole; 5-hydroxyindole; 6-hydroxyindole; 2,6-diaminopyridine and 2-amino-3-hydroxypyridine.

Most preferred primary intermediates include:

p-Phenylenediamine derivatives such as: p-toluenediamine; p-phenylenediamine; N,N-bis(2-hydroxyethyl)-p-phenylenediamine and 2-hydroxyethyl-p-phenylenediamine;

p-Aminophenol derivatives such as: p-aminophenol; p-methylaminophenol; 3-methyl-p-aminophenol and 1-(5-amino-2-hydroxyphenyl)-ethane-1,2-diol;

Ortho-developers such as: o-aminophenol; 1,2,4-trihydroxybenzene; 2-ethylamino-p-cresol; 5-methyl-2-aminophenol; 6-methyl-2-aminophenol and 2-amino-5-acetaminophenol.

Most preferred couplers include:

Phenols, resorcinol and naphthol derivatives such as: 2-methyl-1-naphthol; 1-acetoxy-2-methylnaphthalene; resorcinol; 4-chlororesorcinol; 1-naphthol and 2-methylresorcinol;

m-Phenylenediamines such as: 2,4-diaminophenoxyethanol; 2-amino-4-hydroxyethylamino anisole and 4,6-bis(2-hydroxyethoxy)-m-phenylenediamine; and Heterocyclic derivatives such as: 4,5-diamino-1-methyl-pyrazole: 1-phenyl-3-methyl-5-pyrazolone; 2-amino-3-hydroxypyridine and 6-hydroxyindole.

Preferred combinations employing 1-(2,5-diaminophenyl) ethane-1,2-diol as a p-phenylenediamine replacement include combinations 1–24 set forth in Table 1 which follows:

Combination 1 of Table 1 is a mixture of 1-(2,5-diaminophenyl) ethane-1,2-diol; 2-[(4-aminophenyl)-(2-hydroxy-ethyl)-amino]-ethanol; 2-amino-phenol; benzene-1,3-diol; naphthalen-1-ol; 3-amino-phenol; and 4-amino-phenol.

In reading Table 1, reading down the column headed 2, the components of combination 2 are indicated by x'es.

The composition of each of the remaining combinations is similarly determined.

TABLE 1

COMBINATIONS

| Structure | IUPAC Name | Name | 1 | 2 | 3 | 4 | 5 | 6 | 7 | 8 | 9 | 10 | 11 | 12 |
|---|---|---|---|---|---|---|---|---|---|---|---|---|---|---|
| 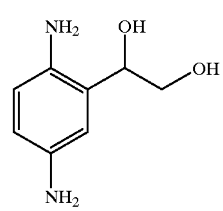 | 1-(2,5-Diamino-phenyl)-ethane-1,2-diol | 1-(2,5-Diaminophenyl)-ethylene glycol | X | X | X | X | X | X | X | X | X | X | X | X |
| 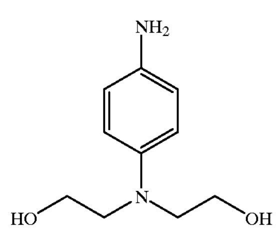 | 2-[(4-Amino-phenyl)-(2-hydroxy-ethyl)-amino]-ethanol | N,N-Bis(2-hydroxyethyl)-p-phenylene-diamine | X | X | X | X | X | X | X | X | X | X | X | X |
| 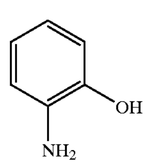 | 2-Amino-phenol | o-Aminophenol | X | X | X | X | X | X | | | | | | |

TABLE 1-continued

| | | COMBINATIONS | | | | | | | |
|---|---|---|---|---|---|---|---|---|---|
| 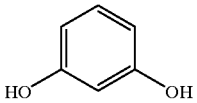 | Benzene-1,3-diol | Resorcinol | X | X | X | X | X | X | |
| 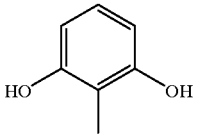 | 2-Methyl-benzene-1,3-diol | 2-Methyl-resorcinol | | X | X | X | X | X | X |
| 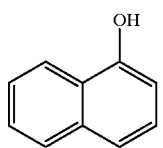 | Naphthalen-1-ol | 1-Naphthol | X | X | X | X | X | X | |
| 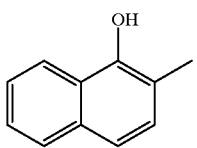 | 2-Methyl-naphthalen-1-ol | 2-Methyl-1-naphthol | | X | X | X | X | X | X |
| 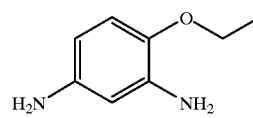 | 2-(2,4-Diamino-phenoxy)-ethanol | 2,4-diamino-phenoxyethanol | | | X | X | X | X | X | X |
| 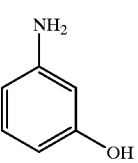 | 3-Amino-phenol | m-Aminophenol | X | X | X | X | X | X | |
| 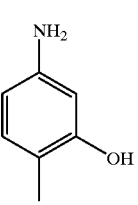 | 5-Amino-2-methyl-phenol | 2-Hydroxy-4-aminotoluene | | X | X | X | X | X | X |
| 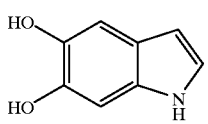 | 1H-Indole-5,6-diol | 5,6-Dihydroxy-indole | | | | | | | |
| 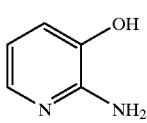 | 2-Amino-pyridin-3-ol | 2-Amino-3-hydroxypyridine | | | | | | | |

TABLE 1-continued

| | | COMBINATIONS | | | | | | | | | | | | |
|---|---|---|---|---|---|---|---|---|---|---|---|---|---|
| Structure | 4-Amino-phenol | p-Aminophenol | X | X | | | X | X | | | | | | |
| Structure | 4-Amino-3-methyl-phenol | 3-Methyl-p-aminophenol | | | X | X | | | X | X | | | | |
| Structure | 1-(5-Amino-2-hydroxy-phenyl)-ethane-1,2-diol | 1-(5-Amino-2-hydroxy-phenyl)-ethane-1,2-diol | | | | | X | X | | | X | X | | |

| Structure | IUPAC Name | Name | 13 | 14 | 15 | 16 | 17 | 18 | 19 | 20 | 21 | 22 | 23 | 24 |
|---|---|---|---|---|---|---|---|---|---|---|---|---|---|---|
| Structure | 1-(2,5-Diamino-phenyl)-ethane-1,2-diol | 1-(2,5-Diaminophenyl)-ethylene glycol | X | X | X | X | X | X | X | X | X | X | X | X |
| Structure | 2-[(4-Amino-phenyl)-(2-hydroxy-ethyl)-amino]-ethanol | N,N-Bis(2-hydroxyethyl)-p-phenylene-diamine | X | X | X | X | X | X | X | X | X | X | X | X |
| Structure | 2-Amino-phenol | o-Aminophenol | | | | | | | | | | | | |
| Structure | Benzene-1,3-diol | Resorcinol | X | | X | | X | | X | | X | | X | |

TABLE 1-continued

COMBINATIONS

| | | | | | | | | | |
|---|---|---|---|---|---|---|---|---|---|
| 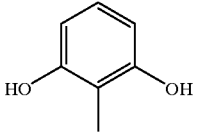 | 2-Methyl-benzene-1,3-diol | 2-Methyl-resorcinol | | X | X | X | X | X | X |
| 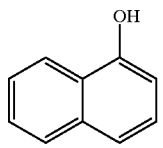 | Naphthalen-1-ol | 1-Naphthol | X | X | X | X | X | | |
| 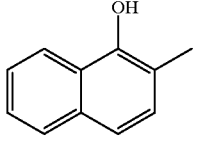 | 2-Methyl-naphthalen-1-ol | 2-Methyl-1-naphthol | | X | X | X | X | X | X |
| 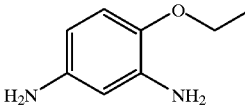 | 2-(2,4-Diamino-phenoxy)-ethanol | 2,4-diamino-phenoxyethanol | | | | | | | |
| 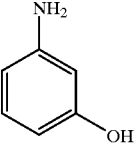 | 3-Amino-phenol | m-Aminophenol | X | | X | X | X | X | X |
| 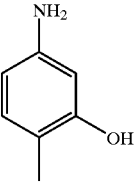 | 5-Amino-2-methyl-phenol | 2-Hydroxy-4-aminotoluene | | X | X | X | X | X | X |
| 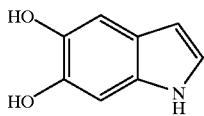 | 1H-Indole-5,6-diol | 5,6-Dihydroxy-indole | X | X | X | X | X | X | |
| 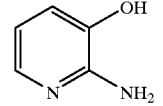 | 2-Amino-pyridin-3-ol | 2-Amino-3-hydroxypyridine | | | | X | X | X | X X X |
| 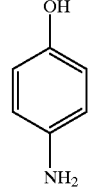 | 4-Amino-phenol | p-Aminophenol | X | X | | | X | X | |

TABLE 1-continued

| COMBINATIONS | | | | | | | |
|---|---|---|---|---|---|---|---|
| 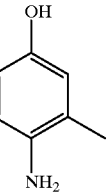 | 4-Amino-3-methyl-phenol | 3-Methyl-p-aminophenol | X | X | | X | X |
| 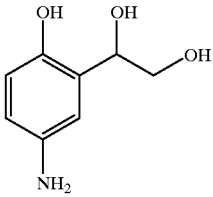 | 1-(5-Amino-2-hydroxy-phenyl)-ethane-1,2-diol | 1-(5-Amino-2-hydroxy-phenyl)-ethane-1,2-diol | | | X | X | X | X |

3. General dyeing procedure:

The test composition (according to Table 2 and Table 3) is mixed with 100 g of 20 volume hydrogen peroxide. The resulting mixture is applied on gray hair and permitted to remain in contact with the hair for 30 minutes. The dyed hair is then shampooed and rinsed with water and dried.

TABLE 2

Composition for Dyeing Hair Red

| Ingredients | Example 1 WT % | Example 2 WT % | Example 3 WT % | Example 4 WT % | Example 5 WT % |
|---|---|---|---|---|---|
| Cocamidopropyl betaine | 17.00 | 17.00 | 17.00 | 17.00 | 17.00 |
| Ethanolamine | 2.00 | 2.00 | 2.00 | 2.00 | 2.00 |
| Oleic acid | 0.75 | 0.75 | 0.75 | 0.75 | 0.75 |
| Citric acid | 0.10 | 0.10 | 0.10 | 0.10 | 0.10 |
| Ammonium hydroxide | 5.00 | 5.00 | 5.00 | 5.00 | 5.00 |
| Behentrimonium chloride | 0.50 | 0.50 | 0.50 | 0.50 | 0.50 |
| Sodium sulfite | 0.10 | 0.10 | 0.10 | 0.10 | 0.10 |
| EDTA | 0.10 | 0.10 | 0.10 | 0.10 | 0.10 |
| Erythorbic acid | 0.40 | 0.40 | 0.40 | 0.40 | 0.40 |
| 1-(2,5-Diaminophenyl)ethane-1,2-diol | 2.66 | 2.66 | 2.00 | 0.50 | 0.50 |
| 4-Aminophenol | 0.92 | | | 2.50 | 2.50 |
| 3-Methyl-p-aminophenol | | 1.20 | | | |
| 2-Methyl-p-aminophenol | | | 1.75 | | |
| 2-Methyl-5-aminophenol | 1.54 | | 1.60 | 1.00 | 1.00 |
| 2-Methyl-5-hydroxethyl aminophenol | | 0.75 | | | |
| 2-Amino-5-methylphenol | | | 0.10 | | |
| 1-Naphthol | | | | 1.50 | |
| 2-Methyl-1-naphthol | | | | | 1.50 |
| Water | qs to 100 | qs to 100 | qs to 100 | qs to 100 | qs to 100 |
| Color obtained on gray hair: | Dark Red | Burgundy Red | Bright Red | Bright Red | Bright Red |

TABLE 3

Composition for Dyeing Hair Black to Brown

| Ingredients | Example 6 WT % | Example 7 WT % | Example 8 WT % | Example 9 WT % | Example 10 WT % |
|---|---|---|---|---|---|
| Cocamidopropyl betaine | 17.00 | 17.00 | 17.00 | 17.00 | 17.00 |
| Ethanolamine | 2.00 | 2.00 | 2.00 | 2.00 | 2.00 |
| Oleic acid | 0.75 | 0.75 | 0.75 | 0.75 | 0.75 |
| Citric acid | 0.10 | 0.10 | 0.10 | 0.10 | 0.10 |
| Ammonium hydroxide | 5.00 | 5.00 | 5.00 | 5.00 | 5.00 |
| Behentrimonium chloride | 0.50 | 0.50 | 0.50 | 0.50 | 0.50 |
| Sodium sulfite | 0.10 | 0.10 | 0.10 | 0.10 | 0.10 |
| EDTA | 0.10 | 0.10 | 0.10 | 0.10 | 0.10 |
| Erythorbic acid | 0.40 | 0.40 | 0.40 | 0.40 | 0.40 |
| 1-(2,5-Diaminophenyl)ethane-1,2-diol | 3.00 | 1.00 | 2.00 | 0.05 | 0.05 |

TABLE 3-continued

Composition for Dyeing Hair Black to Brown

| Ingredients | Example 6 WT % | Example 7 WT % | Example 8 WT % | Example 9 WT % | Example 10 WT % |
|---|---|---|---|---|---|
| N,N-Bis(2-hydroxyethyl)-p-phenylenediamine | 1.00 | 1.00 | .75 | | 0.05 |
| 1-(4-Aminophenyl)pyrrolidine | | 1.00 | | | |
| 4-Aminophenol | | | | 0.10 | 0.05 |
| 2-Aminophenol | | | | 0.10 | 0.10 |
| Resorcinol | 2.00 | 2.00 | | | |
| 2-Methylresorcinol | | | 1.00 | 0.20 | 0.20 |
| m-Aminophenol | 1.50 | 0.80 | 0.80 | 0.05 | 0.10 |
| 2,4-Diaminophenoxyethanol hydrochloride | | 0.50 | | | |
| 4,6-Bis(2-hydroxyethoxy)-m-phenylenediamine | 2.00 | | | | |
| 2-Amino-3-hydroxypyridine | | 0.50 | | | |
| 1-Naphthol | 1.00 | | | 0.03 | 0.02 |
| 2-Methyl-1-naphthol | | | 0.25 | | |
| Water | qs to 100 | qs to 100 | qs to 100 | qs to 100 | qs to 100 |
| Color obtained on gray hair: | Black | Dark Brown | Medium Brown | Golden Blonde | Ash Blonde |

What is claimed is:

1. 1-(2,5-diaminophenyl) ethylene glycol.

2. An oxidative hair dye composition comprising 1-(2,5-diaminophenyl) ethylene glycol as a primary intermediate and a cosmetically acceptable vehicle.

3. The composition of claim 2 further comprising one or more additional primary intermediates and at least one coupler.

4. The composition of claim 3 wherein the additional primary intermediate is selected from the group consisting of p-phenylene diamine; p-toluenediamine; N,N-bis(2-hydroxyethyl)-p-phenylenediamine; p-methylaminphenol; 3-methyl-p-aminophenol, 5-methyl 2-aminophenol, and mixtures thereof.

5. The composition of claim 3 wherein the coupler is selected from the group consisting of 2,4-diaminophenoxyethanol; 4,5-diamino-1-methyl pyrazole, 2-amino-4-hydroxyethyl amino anisole, and mixtures thereof.

6. An oxidative hair dye composition comprising 1-(2,5-diaminophenyl) ethylene glycol as a first primary intermediate, at least one coupler and a cosmetically acceptable vehicle, the first primary intermediate and the at least one coupler reacting in the presence of an oxidizing agent to provide a tinctorially effective amount of the oxidative hair dye.

7. The composition of claim 6 further comprising a second primary intermediate selected from the group consisting of p-phenylene diamine; p-toluenediamine; N,N-bis (2-hydroxyethyl)-p-phenylenediamine; p-methylaminphenol; 3-methyl-p-aminophenol, 5-methyl 2-aminophenol, and mixtures thereof, the first and second primary intermediates and the at least one coupler reacting in the presence of an oxidizing agent to provide a tinctorially effective amount of the oxidative hair dye.

8. The composition of claim 6 further comprising a coupler selected from the group consisting of 2,4-diaminophenoxyethanol; 4,5-diamino-1-methyl pyrazole, and 2-amino-4-hydroxyethyl amino anisole, and mixtures thereof.

9. The composition of claim 6 wherein a dark brown or black shade is obtained when the coupler is a metaphenylenediamine.

10. The composition according to claim 9 wherein the metaphenylenediamine is selected from the group consisting of m-phenylenediamine, 2,4-diaminophenoxyethanol 4,6-bis(2-hydroxyethoxy)-m-phenylenediamine, and mixtures thereof.

11. The composition according to claim 9 wherein the 1-(2,5-diaminophenyl) ethylene glycol and the metaphenylenediamine are present in the composition in a molar ratio of about 1:1.

12. The composition according to claim 9 wherein the composition contains from about 0.1% to about 2% of the metaphenylenediamine.

13. The composition according to claim 10 wherein the 1-(2,5-diaminophenyl)ethylene glycol and the metaphenylenediamine are present in the composition in a molar ratio of about 1:1.

14. The composition according to claim 10 wherein the composition contains from about 0.1% to about 2% of the metaphenylenediamine.

* * * * *